(12) United States Patent
Petignat et al.

(10) Patent No.: US 11,759,366 B2
(45) Date of Patent: Sep. 19, 2023

(54) DEVICE AND METHOD FOR CLEANING THE EXTERNAL AUDITORY CANAL

(71) Applicant: Guy Petignat, Erlenbach (CH)

(72) Inventors: Guy Petignat, Erlenbach (CH); Thomas Linder, Meggen (CH); Mathias Henseler, Horw (CH); Andreas Meyer, Zollikerberg (CH)

(73) Assignee: Guy Petignat, Erlenbach (CH)

( * ) Notice: Subject to any disclaimer, the term of this patent is extended or adjusted under 35 U.S.C. 154(b) by 86 days.

(21) Appl. No.: 16/971,383

(22) PCT Filed: Feb. 20, 2019

(86) PCT No.: PCT/EP2019/054167
§ 371 (c)(1),
(2) Date: Aug. 20, 2020

(87) PCT Pub. No.: WO2019/162303
PCT Pub. Date: Aug. 29, 2019

(65) Prior Publication Data
US 2021/0085526 A1   Mar. 25, 2021

(30) Foreign Application Priority Data
Feb. 21, 2018  (CH) .................................... 00210/18

(51) Int. Cl.
*A61F 11/00* (2022.01)
*A61M 3/02* (2006.01)

(52) U.S. Cl.
CPC ............. *A61F 11/006* (2013.01); *A61M 3/02* (2013.01)

(58) Field of Classification Search
CPC .......... A61F 11/006; A61F 13/38; A61M 3/02
See application file for complete search history.

(56) References Cited

U.S. PATENT DOCUMENTS

| 4,802,797 A * | 2/1989 | Cole .................... A45D 40/267 401/122 |
| 2010/0312198 A1* | 12/2010 | Guidi .................. A61M 35/006 606/162 |
| 2016/0302973 A1* | 10/2016 | Kraitzer ................ A61F 11/006 |

FOREIGN PATENT DOCUMENTS

| CN | 204352011 | 5/2015 |
| CN | 204468421 | 7/2015 |

(Continued)

*Primary Examiner* — Anh T Dang
(74) *Attorney, Agent, or Firm* — Volpe Koenig

(57) ABSTRACT

A device (1) for cleaning the external auditory canal, which device (1) includes a guide sleeve (30), with a proximal outlet portion (31) for partial insertion into the auditory canal, and an instrumentation rod (10) that can be guided axially through the guide sleeve (30). At a proximal end region, the instrumentation rod (10) has a cleaner (20) with at least one circumferentially extending cleaning element (21) which is elastically expandable in a radial direction. An internal cross section of the proximal outlet portion (31) is smaller than an external cross section of the cleaning element (21) in a radially expanded state. The cleaning element (21) can be arranged inside the proximal outlet portion (31) in a radially compressed state in which the cleaning element (21) is bent in the distal direction towards the longitudinal axis of the instrumentation rod (10), such that the cleaning element (21), on emerging from the proximal outlet portion (31), straightens up in the proximal direction into the radially expanded state. A method for cleaning the external auditory canal using such a device (1) is also provided.

13 Claims, 3 Drawing Sheets

(56) References Cited

FOREIGN PATENT DOCUMENTS

| | | |
|---|---|---|
| CN | 204683905 | 10/2015 |
| CN | 206761827 | 12/2017 |
| WO | 2015083161 | 6/2015 |

* cited by examiner

DEVICE AND METHOD FOR CLEANING THE EXTERNAL AUDITORY CANAL

TECHNICAL FIELD

The present invention relates to a device and a method for cleaning the external auditory canal, in particular for removing earwax from the external auditory canal.

BACKGROUND

To clean the external auditory canal (meatus acusticus externus), it is common to use what are called cotton buds. These are generally formed of a small rod which is made of wood, paper or plastic and which at at least one end has a swab made of cellulose or synthetic fibers. However, the use of cotton buds can have the undesired effect of pushing the earwax in the direction of the eardrum and, with frequent use, can even lead to compaction or solidification of the earwax. Earwax that has solidified in this way can sometimes be removed only by a specialist and quite often causes significant hearing loss.

Various types of devices for cleaning the ears, and designed to avoid these problems, are known from the prior art. For example, US 2010/0312198 A1 describes a cleaner with a radially expandable cleaning element which is arranged at a proximal end portion of an instrumentation rod. The cleaning element can have, for example, an elastically deformable means that can be inserted into the auditory canal in a radially compressed state, for example by being received in a sleeve-like insertion device. Upon subsequent release from the insertion device, the cleaning element transfers, under the effect of elastic restoring forces, to a radially expanded state in which it can extend as far as the inner wall of the auditory canal. In this way, when the cleaning element is subsequently pulled back, any earwax present in the distal direction is conveyed out of the auditory canal. Alternatively, the cleaning element can comprise a material that is able to radially expand by taking up liquid. However, devices of this kind have often proven difficult to handle in practice. They are also rather complex and expensive to produce. Moreover, regions of the external auditory canal that lie very far inward in the proximal direction are only inadequately cleaned.

SUMMARY

The object of the present invention is therefore to make available a cost-effective and easily manageable device for cleaning the external auditory canal, which device effectively prevents earwax from being pushed inward and compacted in the auditory canal and also adequately cleans regions of the external auditory canal that lie very far inward in the proximal direction.

This object is achieved by a cleaning device having one or more of the features described herein. Advantageous embodiments of the invention are described below and in the claims.

According to the invention, the device for cleaning the external auditory canal comprises a guide sleeve with a proximal outlet portion for partial insertion into the auditory canal. The device moreover comprises an instrumentation rod which can be guided axially through the guide sleeve. At a proximal end region, the instrumentation rod has a cleaner with at least one circumferentially extending cleaning element that is elastically expandable in a radial direction. The guide sleeve and the cleaning element are designed in such a way that an internal cross section, in particular a smallest internal cross section, of the proximal outlet portion of the guide sleeve is smaller than an external cross section, in particular a smallest external cross section, of the cleaning element in a radially expanded state. In this way, the cleaning element can be transferred to a radially compressed state when the proximal end region of the instrumentation rod is received or arranged in the proximal outlet portion of the guide sleeve. In this state, the cleaning element has an external cross section that is smaller than the internal cross section of the auditory canal. In adults, the latter is typically in the range of about 4-9 mm, on average about 6-7 mm. Accordingly, the external cross section of the cleaning element in the radially compressed state, hence the internal cross section, in particular the smallest internal cross section, of the proximal outlet portion preferably has a diameter of about 2-4 mm. Consequently, the radially compressed state advantageously serves for inserting the cleaning element, together with the guide sleeve, at least partially into the external auditory canal, without earwax being pushed forward in the proximal direction by the compressed cleaning element or even being compacted.

According to the invention, it has been found that, in many of the solutions known from the prior art, the often only inadequate cleaning of regions of the external auditory canal lying far to the inside is caused by the fact that these cleaning elements, upon transfer from the compressed state to the expanded state inside the auditory canal, do not expand exclusively in a radial direction but at the same time experience a movement in a distal direction. In particular, in some of the known solutions, the cleaning element, upon transfer to the expanded state, for example during withdrawal of a guide sleeve surrounding them, fold away from the center axis of the auditory canal in the distal direction, i.e. in the direction of the ear opening. In doing so, the cleaning elements contact the inner wall of the auditory canal only at a position further back than the intended original insertion depth, and they therefore do not exert their cleaning action at the original depth of insertion.

Accordingly, the present invention is characterized in that the at least one cleaning element of the cleaner can be arranged inside the proximal outlet portion in a radially compressed state in which the cleaning element is bent in the distal direction toward the longitudinal axis of the instrumentation rod. This has the advantageous effect that the cleaning element, on emerging from the proximal outlet portion, straightens into the radially expanded state in the proximal direction, i.e. toward the ear interior or in the direction of the eardrum. The emergence of the cleaning element from the proximal outlet portion can preferably be effected by advancing the instrumentation rod in the proximal direction through the guide sleeve via the proximal outlet portion into the external auditory canal. The cleaning element, bent in the distal direction toward the longitudinal axis of the instrumentation rod, straightens to the expanded state only after it has emerged completely from the outlet portion. In this way, a much greater depth of insertion in the proximal direction can advantageously be achieved, without earwax being pushed forward or compacted by the still compressed cleaning element. Compaction of earwax is avoided in particular by the fact that the cleaning element comes to the radially expanded state, and thus optionally into contact with the inner wall of the auditory canal, only when the maximum desired depth of insertion of the instrumentation rod into the auditory canal has been reached. This greatly simplifies the handling and safety of the cleaning device.

As regards the definitions used here, the terms "proximal", "distal" and "radial" are by reference to the anatomy of the external auditory canal. Accordingly, "proximal" denotes a direction toward the ear interior or the eardrum, and "distal" denotes a direction toward the ear opening. The term "radial" denotes a direction extending transversely, in particular perpendicularly, with respect to the center axis of the external auditory canal. Correspondingly, the proximal end portion of the instrumentation rod and the proximal outlet portion of the guide sleeve refer in each case to those portions which, during use of the device according to the invention, in particular during insertion into the external auditory canal, are facing toward the ear interior or the eardrum.

According to an advantageous embodiment of the invention, the cleaning device has a brush. Brush-like cleaning devices or means are particularly suitable for cleaning the ears, not least because of the flexibility of the bristles and the associated low risk of injury. Moreover, brush-like cleaning devices or means are particularly easy to transfer to a radially compressed state by bending of the bristles. Alternatively, instead of bristles, it is also possible to use flexible disks or circle segments, for example made of plastic.

According to a particularly advantageous embodiment, the at least one cleaning element of the cleaning device can have at least one peripheral brush ring composed of a plurality of circumferentially arranged bristles. Preferably, in the radially freely expanded state, the bristles extend outward from the instrumentation rod transversely, in particular perpendicularly with respect to the longitudinal axis of the instrumentation rod. Particularly preferably, the bristles of a brush ring are arranged in an axial plane with respect to the longitudinal axis of the instrumentation rod. In particular, the bristles of a brush ring can be arranged on a circular cross section or can form a circular brush disk. Preferably, the instrumentation rod has between 4 and 10 brush rings or brush disks. In a brush ring, at least three, in particular at least four, preferably at least five, particularly preferably at least six bristles can be arranged circumferentially around the instrumentation rod. For example, a brush ring can have five or six bristles. The bristles are for example plastic bristles, for example bristles made of at least one polymer, polyurethane or polypropylene or rubber. The diameter or the thickness can be between 0.2 and 0.6 mm, preferably between 0.35 and 0.5 mm. The diameter of the brush can be between 8 and 12 mm, preferably 10 mm. The length of the bristles is preferably 4 to 5 mm. Moreover, the bristles can be flocked with cotton at the radial ends. A plurality of bristles can be combined to form a bristle tuft. A plurality of such bristle tufts can be arranged circumferentially on the proximal end portion of the instrumentation rod in order to form at least one brush ring.

The bristles, flexible disks or circle segments can at the same time be injection molded to the instrumentation rod.

According to a further advantageous embodiment of the invention, the instrumentation rod has a cleaner which comprises a plurality of cleaning elements, in particular a plurality of brush rings. The plurality of cleaning elements, in particular the plurality of brush rings, are preferably arranged in axial distribution along the proximal end portion. In this way, the cleaning action of the device is advantageously enhanced.

Furthermore, the external cross section of a cleaner consisting of a plurality of cleaning elements, for example a brush, in particular a brush having a plurality of brush rings spaced axially apart from one another, can decrease in the distal direction, preferably conically or in steps. Such a cleaner can thus have a conical or stepped shape decreasing in the distal direction. Accordingly, in such an embodiment, the radial dimensions of the plurality of cleaning elements, in particular the diameters of the brush rings and the lengths of the bristles of the respective brush rings, can decrease in the distal direction along the proximal end portion. This has the effect that all of the cleaning element straighten to the expanded state only when the cleaning element arranged furthest proximally along the proximal end portion has emerged completely from the proximal end portion. Advantageously, the maximum depth of insertion of the proximal end portion or of the whole cleaner into the auditory canal is in this way increased.

Furthermore, the bristles in a cleaner having a plurality of brush rings spaced axially apart from one another can be arranged such that the bristles of adjacent brush rings are circumferentially offset relative to each other. This likewise enhances the cleaning action.

Moreover, provision can be made that the bristles are arranged along the proximal end portion in such a way that a plurality of bristles, preferably two to three bristles, come to overlap each other in the compressed state. In this way, a particularly high degree of compression can advantageously be achieved, as a result of which the danger of undesired pushing or compaction of earwax is minimized.

According to a further advantageous embodiment of the invention, the guide sleeve, in particular the outlet portion, can have in the proximal direction a hyperbolic, parabolic or conical or a hyperbolically, parabolically or conically shaped tapering of the external cross section. For example, the proximal outlet portion can have an outer cone. The hyperbolic, parabolic or conical geometry of the tapering has the effect that the depth of insertion of the outlet portion varies depending on the width of the auditory canal and in particular is automatically limited, and therefore the risk of injury is reduced. In narrow auditory canals, the guide sleeve, in particular the outlet portion, can penetrate less deeply than in wide auditory canals. Moreover, the outer cone provides an abutment for the guide sleeve upon application or partial insertion into the auditory canal, which makes the overall device easier to handle. In particular, the device can in this way be used with one hand.

In addition to the proximal outlet portion, the guide sleeve can have a distal, preferably cylindrical depot portion for receiving the at least one cleaning element in the radially expanded state. This has the advantage that the at least one cleaning element is stored in the radially expanded state, i.e. in the deployed state, between production and use, for example during storage and sale, as a result of which fatigue of the elastic material properties is avoided.

At the same time, the surrounding depot portion of the insertion sleeve protects the cleaning element from harmful external influences, for example contamination. The depot portion of the insertion sleeve is designed such that a smallest internal cross section of the distal depot portion is larger than the largest external cross section of the proximal end region in the radially expanded state of the cleaning element.

According to a further embodiment of the invention, the guide sleeve, in particular the outlet portion, can have a tapering of the internal cross section in the proximal direction, for example a hyperbolically, parabolically or conically shaped tapering of the internal cross section. In particular, the outlet portion can be designed as a funnel or with a funnel shaper or nozzle shape. It is thus possible in a particularly simple manner to arrange the at least one cleaning element inside the proximal outlet portion in the radially compressed state and to ensure that the cleaning element in the radially compressed state is arranged inside the proximal outlet portion such that it can bend in the distal direction toward the longitudinal axis of the instrumentation rod as per the invention. Moreover, the conical tapering facilitates the transfer of the cleaning element from the depot portion into the outlet portion. Furthermore, the conical tapering of the internal cross section of the outlet portion can advantageously serve as a mechanical abutment for the instrumentation rod. In this way, the depth of insertion of the proximal end portion of the instrumentation rod and of the cleaning element into the auditory canal can be limited by particularly simple technical means. For this purpose, the instrumentation rod can have a radially widened portion, for example.

It is moreover advantageous if the instrumentation rod is elastic or flexible. In this way, the instrumentation rod can adapt to the anatomical course of the auditory canal during insertion, as a result of which injury to the auditory canal is avoided.

Provision can furthermore be made that the instrumentation rod has a blunt or flat termination at the proximal end of the proximal end region. In particular, the instrumentation rod itself can have a blunt or flat termination. In addition, the at least one cleaning element can be designed such that, in the radially expanded state, it forms a flat termination extending substantially perpendicularly with respect to the longitudinal axis of the instrumentation rod, for example in the form of a plane circular surface that is formed by a brush ring. In this way too, injury to the auditory canal and in particular to the eardrum is avoided.

The length of the instrumentation rod corresponds at least to the maximum desired or anatomically predefined depth of insertion. In particular, the instrumentation rod can have an outlet length of 8 to 20 mm, preferably of 10 to 12 mm, which is displaceable in the proximal direction from the proximal outlet portion of the guide sleeve. The diameter of the cleaning element can be between 5 mm and 14 mm, preferably 10 mm. Its cross-sectional shape can be cylindrical or elliptical, depending on the anatomy of the auditory canal.

According to a further embodiment of the invention, the instrumentation rod can have at least one inner channel which, in the proximal end region, opens into one or more outlet openings. The inner channel can advantageously be used for application of liquids, in particular irrigating and/or cleaning liquids, creams, almond oil or the like. Liquids and creams can also be advantageously stored in the above-described depot portion, in order to be applied from there into the auditory canal via the at least one inner channel and distributed in the auditory canal with the aid of the cleaning element, for example a brush.

Furthermore, the device can have at a distal end of the instrumentation rod, or adjacent to a distal end of the instrumentation rod, a handle for actuating the instrumentation rod.

The cleaning device according to the invention is preferably produced from plastic. In particular, the cleaning device can be designed as a disposable device. For this purpose, it may be advantageous if the device is produced from biodegradable material, for example bioplastics.

The device according to the invention is intended primarily for cleaning the external auditory canal of humans, but it can also be used to clean the external auditory canal of animals, for example dogs or cats.

According to a particularly preferred embodiment, the whole device is designed in the form of a disposable syringe.

In this case, a syringe barrel is preferably formed by a distal, in particular cylindrical depot portion of the guide sleeve according to the invention (in particular as described above), which serves to receive the at least one cleaning element in the radially expanded state. Adjoining the depot portion, the syringe barrel has a proximal outlet portion according to the invention. The outlet portion preferably has a tapering of the internal and/or external cross section, for example a hyperbolic, parabolic or conical or hyperbolically, parabolically or conically shaped tapering of the external cross section and/or a hyperbolic, parabolic or conical or hyperbolically, parabolically or conically shaped tapering of the internal cross section. A syringe plunger is guided with a sliding movement in the syringe barrel. At its proximal end, the syringe plunger has a cylinder disk for guiding the syringe plunger with a sliding movement, preferably a sealing sliding movement, in the syringe barrel. From the cylinder disk, an instrumentation rod according to the invention with the cleaner extends in the proximal direction along the plunger axis. The cylinder disk moreover preferably serves as a means for limiting the depth of insertion of the instrumentation rod since, when advanced in the proximal direction, it comes into abutment with the conical tapering of the internal cross section of the proximal outlet portion. A further means for limiting the depth of insertion is provided by a radially widened support face at the distal end of the syringe plunger. This support face preferably serves as a support face for the thumb with which the plunger can be displaced in the proximal direction during the insertion of the instrumentation rod from the depot portion into the auditory canal via the outlet portion. During the advance in the proximal direction, the radially widened support face comes into abutment with the distal end of the syringe barrel. Two mutually opposite wings, each extending in the radial direction, are preferably provided at the distal end of the syringe barrel, which wings serve as a support for the index finger and middle finger, when advancing the plunger, to provide support counter to the advancing force.

Instead of a support for the thumb, as described above, other means are also conceivable for operating the instrumentation rod or the syringe plunger. Thus, the device can preferably have a handle at the distal end of the syringe plunger or of the instrumentation rod, which handle can be grasped with thumb and index finger, for example, in order to actuate the syringe plunger or the instrumentation rod. The use of such a handle is distinguished in particular by the fact that it not only permits good control of the syringe plunger or the instrumentation rod during the advance in the proximal direction but also, compared to a support face for the thumb, makes the withdrawal in the distal direction considerably easier. Moreover, when using such a handle, a radially widened support face can also be provided at the distal end of the syringe plunger and serves as an abutment with the distal end of the syringe barrel in order to limit the depth of insertion. In this configuration, the handle can adjoin the radially widened support face in the distal direction. Preferably, the handle is injection molded to the distal end of the syringe plunger, particularly to the radially widened support face, if the latter is present.

A further aspect of the invention relates to a method for cleaning the external auditory canal using a device according to the invention, in particular as described above. The method is characterized by the following steps:
 a. inserting the proximal outlet portion of the guide sleeve into the external auditory canal as far as a predefined depth of insertion, in a first advancing movement;

b. advancing the instrumentation rod in the proximal direction through the guide sleeve via the proximal outlet portion into the external auditory canal, in a second advancing movement, until the at least one cleaning element has transferred from the compressed state to the radially expanded state; and c. simultaneously withdrawing the guide sleeve and the instrumentation rod, in the radially expanded state of the cleaning element, from the external auditory canal in a single joint withdrawal movement.

The invention moreover relates to a further method for cleaning the external auditory canal using a device according to the invention, in particular as described above. The further method is characterized by the following steps:

a. In a single joint advancing movement:
inserting the proximal outlet portion of the guide sleeve into the external auditory canal as far as a predefined depth of insertion and simultaneously advancing the instrumentation rod in the proximal direction through the guide sleeve via the proximal outlet portion into the external auditory canal, until the at least one cleaning element has transferred from the compressed state to the radially expanded state; and b. simultaneously withdrawing the guide sleeve and the instrumentation rod, in the radially expanded state of the cleaning element, from the external auditory canal in a single joint withdrawal movement.

BRIEF DESCRIPTION OF THE DRAWINGS

Further aims, advantages, features and possible uses of the present invention will become clear from the following description of an illustrative embodiment shown in the drawings. Here, all of the features described and/or depicted in the figures, alone or in any desired combination, form the subject matter of the present invention, independently of the combination of said features in the claims or the back-references thereof.

In the drawings.

DETAILED DESCRIPTION

Figure 1:
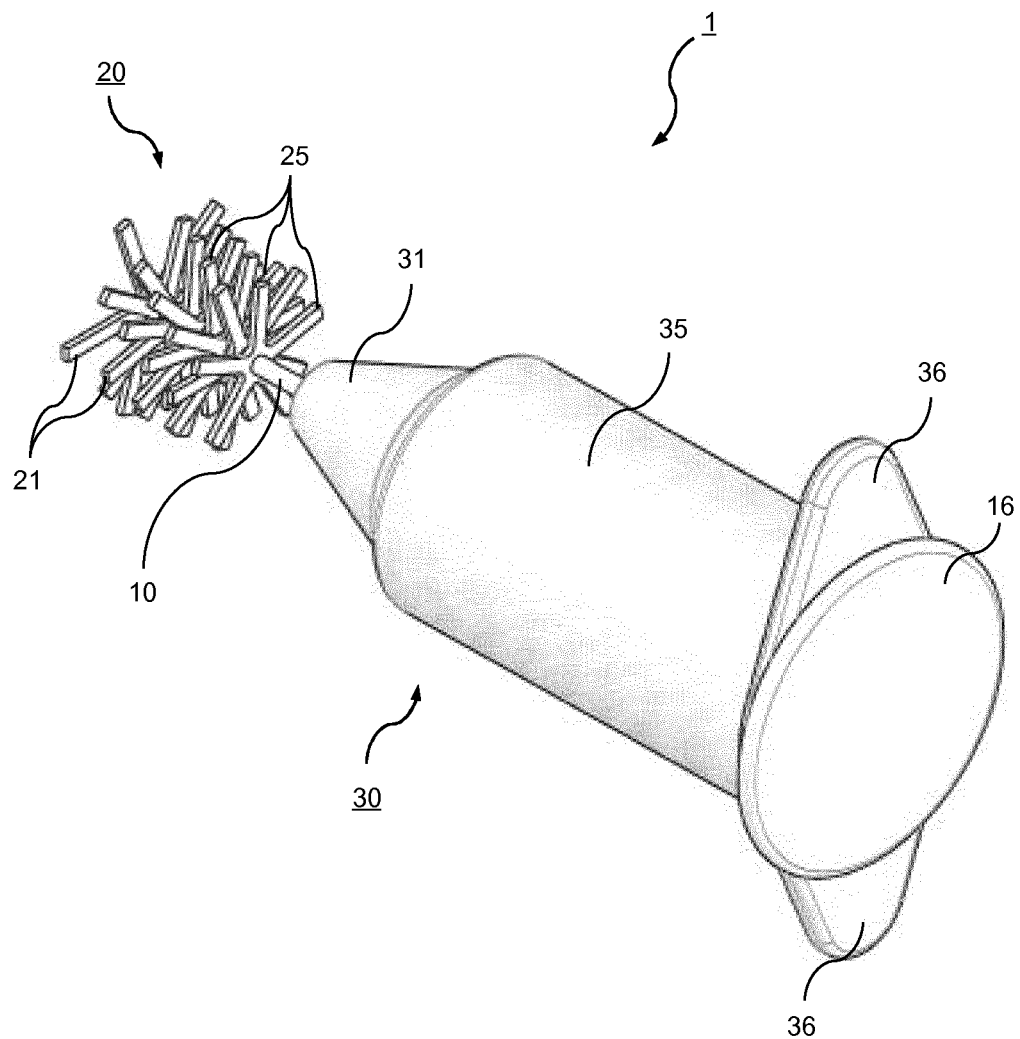
FIG. 1 shows a perspective view of an illustrative embodiment of a device according to the invention for cleaning the external auditory canal.
Figure 2:
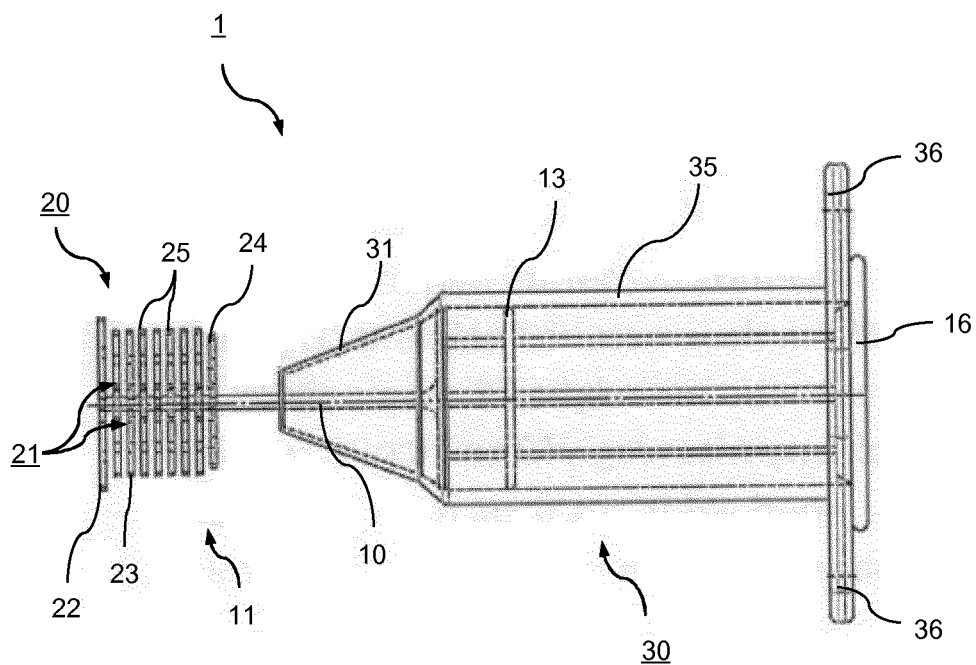
FIG. 2 shows a longitudinal section through the illustrative embodiment of the device according to the invention from FIG. 1.
Figure 3:
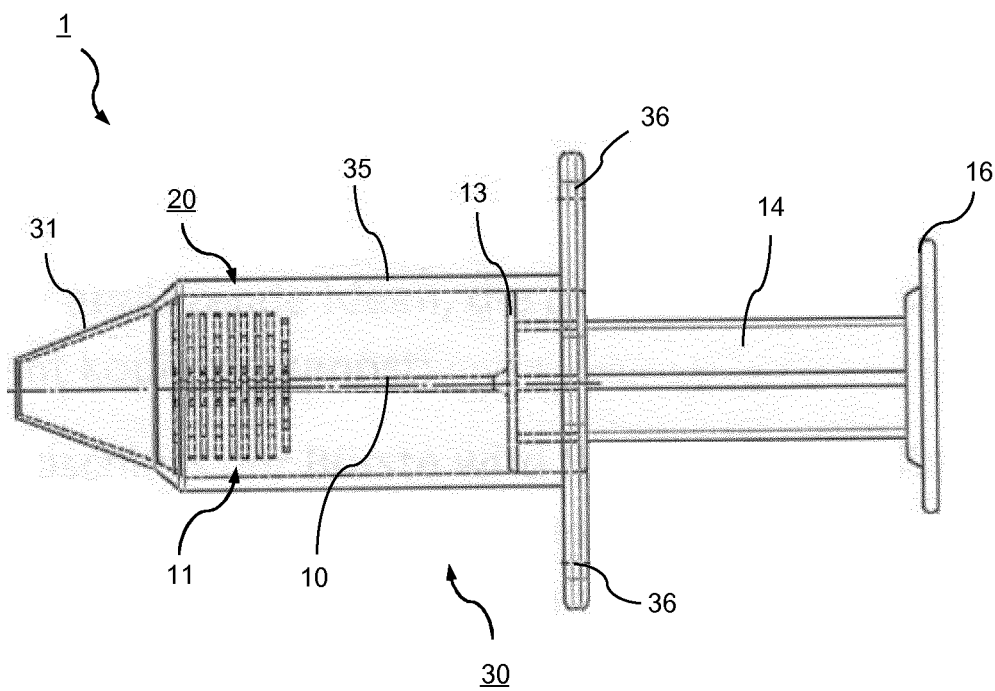
FIG. 3 shows a longitudinal section through the illustrative embodiment of the device according to the invention from FIG. 1 prior to use.

FIGS. 1-3 show a possible illustrative embodiment of a device 1 according to the invention for cleaning the external auditory canal. According to the invention, the device 1 comprises an instrumentation rod 10, at the proximal end region 11 of which is arranged a cleaner 20 with a plurality of circumferentially extending cleaning element 21 that are elastically expandable in a radial direction. In the present illustrative embodiment, the cleaner 20 is a brush for cleaning the external auditory canal. As can be seen in particular from FIGS. 2 and 3, the brush in the present case has a plurality of cleaning elements 21 in the form of a plurality of brush rings 22, 23, 24, for example nine of them, which are arranged on the instrumentation rod 10 in the axial direction (with respect to the longitudinal axis of the instrumentation rod 10) in a distribution along the proximal end region 11. Each brush ring 22, 23, 24 is composed of a plurality of peripherally arranged bristles 25, for example five of them, which in the freely expanded state extend radially outward from the instrumentation rod 10, transversely with respect to the longitudinal axis of the latter. In particular, all the bristles 25 of a brush ring 22, 23, 24 are of equal length and are arranged in an axial plane with respect to the longitudinal axis of the instrumentation rod 10, such that they form a circular brush disk. As is shown in particular in FIG. 1, the plurality of brush rings 22, 23, 24, spaced axially apart from one another, are arranged such that the bristles of adjacent brush rings are circumferentially offset relative to one another. The bristles 25 are preferably plastic bristles. The instrumentation rod is also preferably made of plastic, in particular a flexible plastic, such that it adapts well to the anatomical profile of the ear when inserted into the auditory canal. The proximal end of the end region 11 forms a blunt or flat termination together with the brush ring 22 arranged furthest in the proximal direction, as a result of which damage to the auditory canal and in particular to the eardrum is advantageously avoided. The bristles can be injection molded at one end onto the instrumentation rod 10.

According to the invention, the device 1 further comprises a guide sleeve 30 with a proximal outlet portion 31 for partial insertion into the external auditory canal, through which guide sleeve 30 the instrumentation rod 10 can be introduced together with the cleaner 20 into the auditory canal. In addition to the proximal outlet portion 31, the guide sleeve 30 has a distal, cylindrical depot portion 35 which serves to receive and store the brush-like cleaner 20 in the radially freely expanded state, i.e. in the deployed state. It is thus possible to prevent loss of the elastic material properties of the bristles between production and actual use of the cleaner. For this purpose, the internal cross section of the cylindrical depot portion 35 is larger than the largest external cross section of the brush rings 22, 23, 24 in the radially expanded state. At the same time, the brush is protected from harmful external influences, for example contamination, by the surrounding depot portion 35.

As can be seen in detail in FIGS. 2 and 3, the proximal outlet portion 31 in the present illustrative embodiment is designed in the form of a hollow truncated cone which, in the proximal direction, adjoins the cylindrical depot portion 35. Both the internal cross section and the external cross section of the outlet portion 31 narrow conically in the proximal direction. A hyperbolic or parabolic tapering is also conceivable. Here, the chosen geometry, for example in the present case the outer cone, has the effect that the depth of insertion of the outlet portion 31 is automatically limited according to the width of the auditory canal, and therefore the risk of injury is reduced. Moreover, the outer cone provides an abutment for the guide sleeve upon application or partial insertion into the auditory canal, and this makes the manipulation of the device 1 as a whole easier. In particular, the device can in this way be used with one hand.

According to the invention, the internal cross section of the outlet portion 31 serves to radially compress the brush rings 22, 23, 24 during the advance of the instrumentation rod in the proximal direction from the depot portion in which they are located in the freely expanded, deployed position, i.e. to bring them to a radially compressed state. According to the invention, the compression is effected in such a way that the bristles 25 of all the brush rings 22, 23, 24 within the proximal outlet portion 31 are bent in the distal direction toward the longitudinal axis of the instrumentation rod 10, i.e. they point with the free ends away from the proximal outlet opening of the cone in the direction of the opening cone. Here, the funnel-shaped and in particular conical tapering of the internal cross section facilitates the transfer and compression of the brush rings 22, 23, 24 from the depot portion 35 into the outlet portion 31. Moreover, the conical tapering of the internal cross section can advantageously serve as a mechanical abutment for a radial widening part 13 at a distal end region of the instrumentation rod 10. As is shown in detail in FIGS. 2 and 3, the smallest internal cross section of the proximal outlet portion 31 has, in the region of the proximal outlet opening of the conical outlet portion 31, a significantly smaller diameter than the external cross section of the brush-like cleaner 20 in the freely expanded state. In the present illustrative embodiment, the diameter of the outlet opening of the conical outlet portion 31, hence the diameter of the external cross section of the brush-like cleaner 20 in the radially compressed state, measures approximately 4 mm and is therefore smaller than the internal cross section of the auditory canal which, in adults, is typically in the range of approximately 4 to 9 mm, on average about 7 mm. Thus, the brush-like cleaner 20 can be inserted at least partially into the external auditory canal by advancing the instrumentation rod 10, without coming into contact with the inner wall of the auditory canal and undesirably pushing earwax in the proximal direction.

Since the bristles 25 of the brush rings 22, 23, 24 within the proximal outlet portion 31 in the radially compressed state are bent in the distal direction toward the longitudinal axis of the instrumentation rod 10, it is ensured in particular that the bristles, on emerging from the proximal end portion 31, straighten to the radially expanded state in the proximal direction, i.e. toward the interior of the ear or in the direction of the eardrum. As can be seen in particular from FIG. 2, the bristles 25 of the brush ring 22 arranged furthest forward in the proximal direction are longer than the bristles 25 of the brush ring 24 lying immediately behind. The length of the bristles 25 of the brush rings 23 lying in between is between the length of the bristles 25 of the brush rings 22, 24 lying furthest forward and furthest to the rear. Thus, in the radially expanded state, the brush has an external cross section increasing conically or in steps in the proximal direction. This has the effect that all of the cleaning element straighten to the expanded state only when the cleaning element arranged furthest forward along the proximal end portion has emerged completely from the proximal outlet portion. Advantageously, it is thus possible to achieve a much greater depth of insertion of the cleaning element in the proximal direction, without earwax being pushed forward proximally or compacted by the (still compressed) cleaning element. The latter scenario is avoided in particular by the fact that the cleaning element reaches the radially expanded state, and thus optionally comes into contact with the inner wall of the auditory canal, only when the maximum desired depth of insertion of the instrumentation rod 10 is attained.

In the illustrative embodiment shown in FIGS. 1 to 3, the device 1 as a whole is designed in the form of a disposable syringe, which is distinguished by particularly easy manipulation. A syringe barrel is formed by the cylindrical shape of the depot portion 35, which is adjoined by the conical outlet portion 31 as a kind of outlet nozzle or outlet funnel. A syringe plunger 14 is guided with a sliding movement by means of a cylinder disk 13. From the cylinder disk 13, the instrumentation rod 10 with cleaner 20 extends in the proximal direction along the plunger axis. The cylinder disk 13 moreover serves as a means limiting the depth of insertion of the instrumentation rod 20 into the auditory canal since, when advanced in the proximal direction, it comes into abutment with the inner cone of the proximal outlet portion 31. A further means for limiting the depth of insertion is provided by a radially widened support face 16 at the distal end of the syringe plunger, which support face 16 preferably serves as a support face for the thumb when advancing the plunger 14 in the proximal direction. During the advance in the proximal direction, the radially widened support face 16 comes into abutment with the distal end of the syringe barrel. Two mutually opposite wings 36, each extending in the radial direction, are moreover provided at the distal end of the syringe barrel, which wings 36 serve as a support for the index finger and middle finger, when advancing the plunger, to provide support counter to the advancing force.

Figure 4:
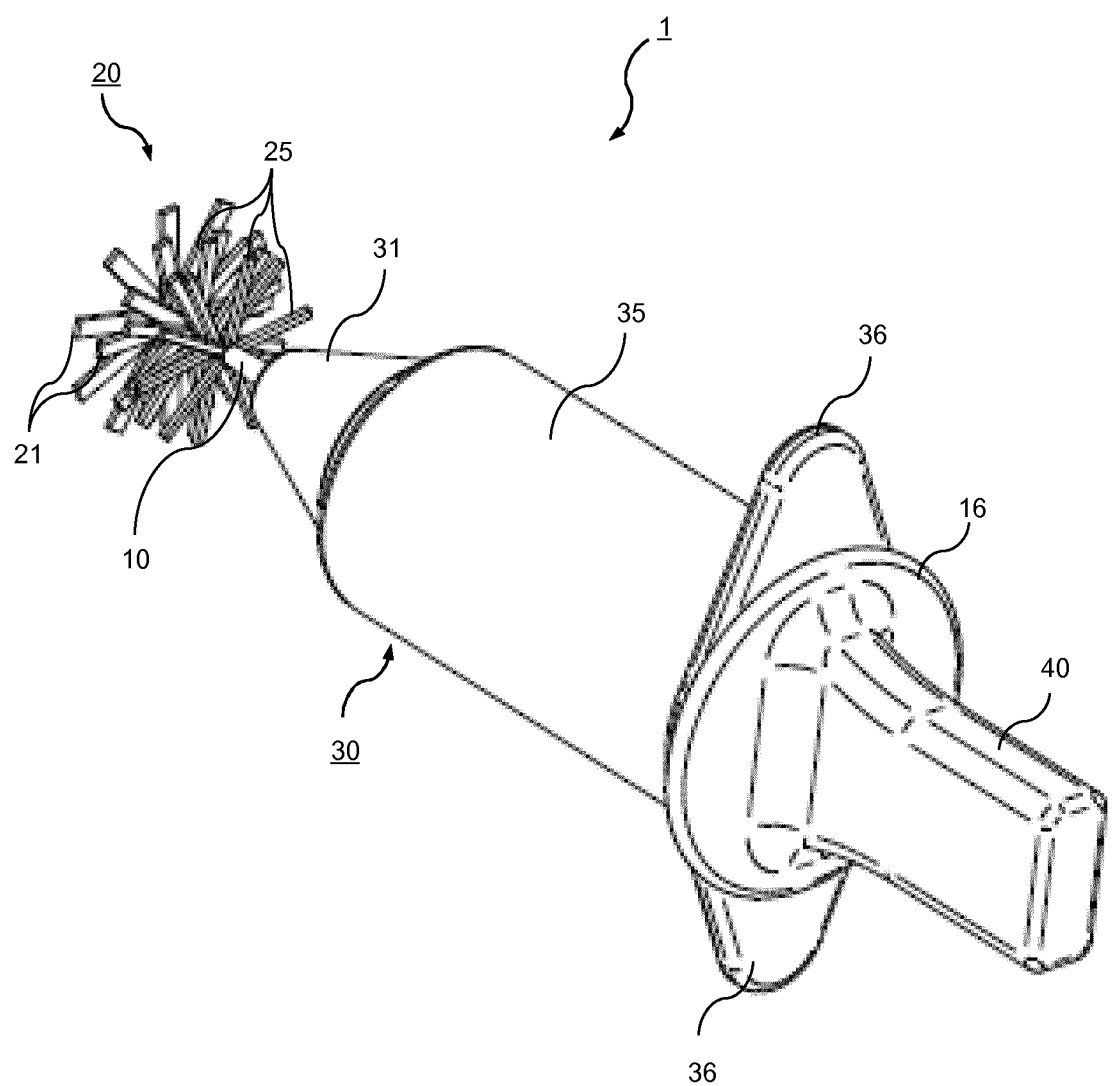
FIG. 4 shows a further illustrative embodiment of a device according to the invention with a handle.

Instead of a support for the thumb, as described above, other means are also conceivable for operating the instrumentation rod or the syringe plunger 14. Thus, according to a further illustrative embodiment of the invention, the device 1, as shown in FIG. 4, can have a handle 40 at the distal end of the syringe plunger 14, which handle 40 can be grasped with thumb and index finger, for example, in order to actuate the syringe plunger 14. The use of such a handle 40 is distinguished in particular by the fact that it not only permits good control of the syringe plunger 14 during the advance in the proximal direction but also, compared to a support face for the thumb, makes the withdrawal in the distal direction considerably easier. Moreover, when using such a handle 40, a radially widened support face 16 can be provided at the distal end of the syringe plunger 14 and serves as an abutment with the distal end of the syringe barrel in order to limit the depth of insertion. In this configuration, the handle 40 can adjoin the radially widened support face 16 in the distal direction. Preferably, the handle 40 is injection molded to the distal end of the syringe plunger 14, particularly to the radially widened support face 16, if the latter present.

With the illustrative embodiments of the device shown here, the cleaning of the auditory canal can in principle be performed according to at least two variants. In a first variant, the whole cleaning device 1 is inserted into the auditory canal in a single movement and is withdrawn again from the auditory canal in a single movement. In particular, in a single joint advancing movement, the guide sleeve 30 can be inserted with the proximal end portion 31 into the external auditory canal as far as a predetermined depth of insertion and at the same time, by advancing of the instrumentation rod 10 in the proximal direction, the brush-like cleaner 20 can be inserted from the depot portion 35 via the proximal end portion 31 into the external auditory canal until the bristles 25 of the brush rings 22, 23, 24 are transferred from the temporarily compressed state to the radially expanded state. The guide sleeve 30 and the instrumentation rod 10 in the radially expanded state of the brush rings 22, 23, 24 can then be withdrawn from the external auditory canal in a single joint movement, whereby any earwax present in the distal direction is conveyed out of the auditory canal.

In a second variant, only the guide sleeve 30 with the proximal outlet portion 31 is initially inserted in a first advancing movement into the auditory canal as far as a predetermined depth of insertion. The brush-like cleaner 20 is preferably still located in the depot portion 35. In a second advancing movement, in which the instrumentation rod 10 is advanced in the proximal direction, the brush-like cleaner 20 is then inserted from the depot portion 35 via the proximal outlet portion 31 into the external auditory canal until the bristles 25 of the brush rings 22, 23, 24 are transferred from the temporarily compressed state to the radially expanded state. Thereafter, as in the first variant, the guide sleeve 30 and the instrumentation rod 10 in the radially expanded state of the bristles 25 are then withdrawn from the external auditory canal in a single joint withdrawal movement.

The invention claimed is:

1. A device (1) for cleaning an external auditory canal, said device (1) comprising:
   a guide sleeve (30) with a proximal outlet portion (31) adapted for partial insertion into the auditory canal,
   an instrumentation rod (10) having a longitudinal axis and which is guidable axially through the guide sleeve (30), the instrumentation rod including a proximal end region (11) that is configured to extend out of the proximal outlet portion in a proximal direction along the longitudinal axis, and a distal direction is defined in an opposite direction from the proximal outlet portion along the longitudinal axis,
   a cleaner (20) located at the proximal end region and having at least one circumferentially extending cleaning element (21) that is elastically expandable in a radial direction, wherein an internal cross section of the proximal outlet portion (31) is smaller than an external cross section of the cleaning element (21) in a radially expanded state,
   the at least one cleaning element (21) is arranged inside the proximal outlet portion (31) in a radially compressed state in which the cleaning element (21) is elastically deflected in a distal direction toward the longitudinal axis of the instrumentation rod (10), such that the at least one cleaning element (21), on emerging from the proximal outlet portion (31), is configured to straighten into the radially expanded state in the proximal direction.

2. The device (1) as claimed in claim 1, wherein the cleaning element (21) has at least one peripheral brush ring (22, 23, 24) comprised of at least one of a plurality of circumferentially arranged bristles (25), flexible disks or circle segments and which, in the radially expanded state, extend outward from the instrumentation rod (10) transversely with respect to the longitudinal axis.

3. The device (1) as claimed in claim 2, wherein the cleaner (20) has a plurality of cleaning elements (21), each comprising at least one of the at least one brush ring (22, 23, 24) which are arranged axially distributed along the proximal end region (11).

4. The device (1) as claimed in claim 3, wherein an external cross section of the cleaner (20) in the radially expanded state, decreases in the distal direction along the proximal end region (11).

5. The device (1) as claimed in claim 1, wherein the guide sleeve (30) has in the proximal direction a conical, hyperbolic or parabolic tapering of an internal cross section thereof.

6. The device (1) as claimed in claim 1, wherein the guide sleeve (30) has in the proximal direction a conical tapering of an external cross section thereof.

7. The device (1) as claimed in claim 1, wherein the guide sleeve (30) has a distal depot portion (35) that receives the at least one cleaning element (21) in the radially expanded state, and a smallest internal cross section of the distal depot portion is larger than a largest external cross section of the proximal end region (11) in the radially expanded state of the cleaning element (21).

8. The device (1) as claimed in claim 1, wherein the instrumentation rod (10) is elastic.

9. The device (1) as claimed in claim 1, wherein the instrumentation rod (10) has at least one inner channel which, in the proximal end region (11), opens into one or more outlet openings.

10. The device (1) as claimed in claim 1, wherein the instrumentation rod (10) has a blunt or flat termination at a proximal end of the proximal end region (11).

11. The device (1) as claimed in claim 1, further comprising, at a distal end of the instrumentation rod (10), or adjacent to a distal end of the instrumentation rod (10), a handle for actuating the instrumentation rod (10).

12. A method for cleaning the external auditory canal using the device (1) as claimed in claim 1, comprising the following steps:
   a. inserting the proximal outlet portion (31) of the guide sleeve (30) into the external auditory canal as far as a predefined depth of insertion, in a first advancing movement;
   b. advancing the instrumentation rod (10) in the proximal direction through the guide sleeve (30) via the proximal outlet portion (31) into the external auditory canal, in a second advancing movement, until the at least one cleaning element (21) has transferred from the compressed state to the radially expanded state; and
   c. simultaneously withdrawing the guide sleeve (30) and the instrumentation rod (10), in the radially expanded state of the cleaning element (21), from the external auditory canal in a single joint withdrawal movement.

13. A method for cleaning the external auditory canal using the device (1) as claimed in claim 1, comprising the following steps:
   a. in a single joint advancing movement:
   inserting the proximal outlet portion (31) of the guide sleeve (30) into the external auditory canal as far as a predefined depth of insertion and simultaneously advancing the instrumentation rod (10) in the proximal direction through the guide sleeve (30) via the proximal outlet portion (31) into the external auditory canal, until the at least one cleaning element (21) has transferred from the compressed state to the radially expanded state; and
   b. simultaneously withdrawing the guide sleeve (30) and the instrumentation rod (10), in the radially expanded state of the cleaning element (21), from the external auditory canal in a single joint withdrawal movement.

\* \* \* \* \*